(12) United States Patent
Fischer, Jr.

(10) Patent No.: US 8,882,751 B2
(45) Date of Patent: Nov. 11, 2014

(54) WIRE GUIDED THROMBECTOMY DEVICE

(75) Inventor: Frank J. Fischer, Jr., Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 1497 days.

(21) Appl. No.: 12/206,931

(22) Filed: Sep. 9, 2008

(65) Prior Publication Data

US 2010/0063488 A1   Mar. 11, 2010

(51) Int. Cl.
*A61B 18/18* (2006.01)
*A61B 18/24* (2006.01)

(52) U.S. Cl.
CPC ..................................... *A61B 18/245* (2013.01)
USPC .............................................................. 606/7

(58) Field of Classification Search
USPC .......... 606/7, 10–17, 113, 114, 127, 128, 159
See application file for complete search history.

(56) References Cited

U.S. PATENT DOCUMENTS

| | | | |
|---|---|---|---|
| 4,207,874 A * | 6/1980 | Choy | 600/108 |
| 4,844,062 A * | 7/1989 | Wells | 606/7 |
| 4,913,142 A * | 4/1990 | Kittrell et al. | 606/7 |
| 5,026,367 A | 6/1991 | Leckrone et al. | |
| 5,114,403 A | 5/1992 | Clarke et al. | |
| 5,135,482 A | 8/1992 | Neracher | |
| 5,147,348 A | 9/1992 | Leckrone et al. | |
| 5,188,634 A | 2/1993 | Hussein et al. | |
| 5,423,805 A * | 6/1995 | Brucker et al. | 606/15 |
| 5,437,659 A | 8/1995 | Leckrone | |
| 5,451,233 A | 9/1995 | Yock | |
| 5,484,433 A * | 1/1996 | Taylor et al. | 606/17 |
| 5,938,645 A | 8/1999 | Gordon | |
| 6,176,855 B1 | 1/2001 | Heckele et al. | |
| 6,183,433 B1 | 2/2001 | Bays | |
| 6,547,779 B2 | 4/2003 | Levine et al. | |
| 2007/0282303 A1 | 12/2007 | Nash et al. | |

FOREIGN PATENT DOCUMENTS

DE           3617019       * 11/1987

\* cited by examiner

*Primary Examiner* — Tuan V Nguyen
(74) *Attorney, Agent, or Firm* — Brinks Gilson & Lione

(57) ABSTRACT

A medical device for removing a thrombus from a blood vessel and a process thereof is presented. The device includes an outer sheath with a plurality of lumens. A wire guide inserted through one of the lumens is used to place the device proximate to a thrombus. An optical fiber placed through a second lumen uses laser input to ablate the thrombus in the distal portion of the second lumen near its distal end. A vacuum coupled to the proximal end of the second lumen is used to remove any ablated residual material. The second lumen may be pivoted around the first lumen to reposition the second lumen proximate to an area of the thrombus that has not yet been ablated.

3 Claims, 4 Drawing Sheets

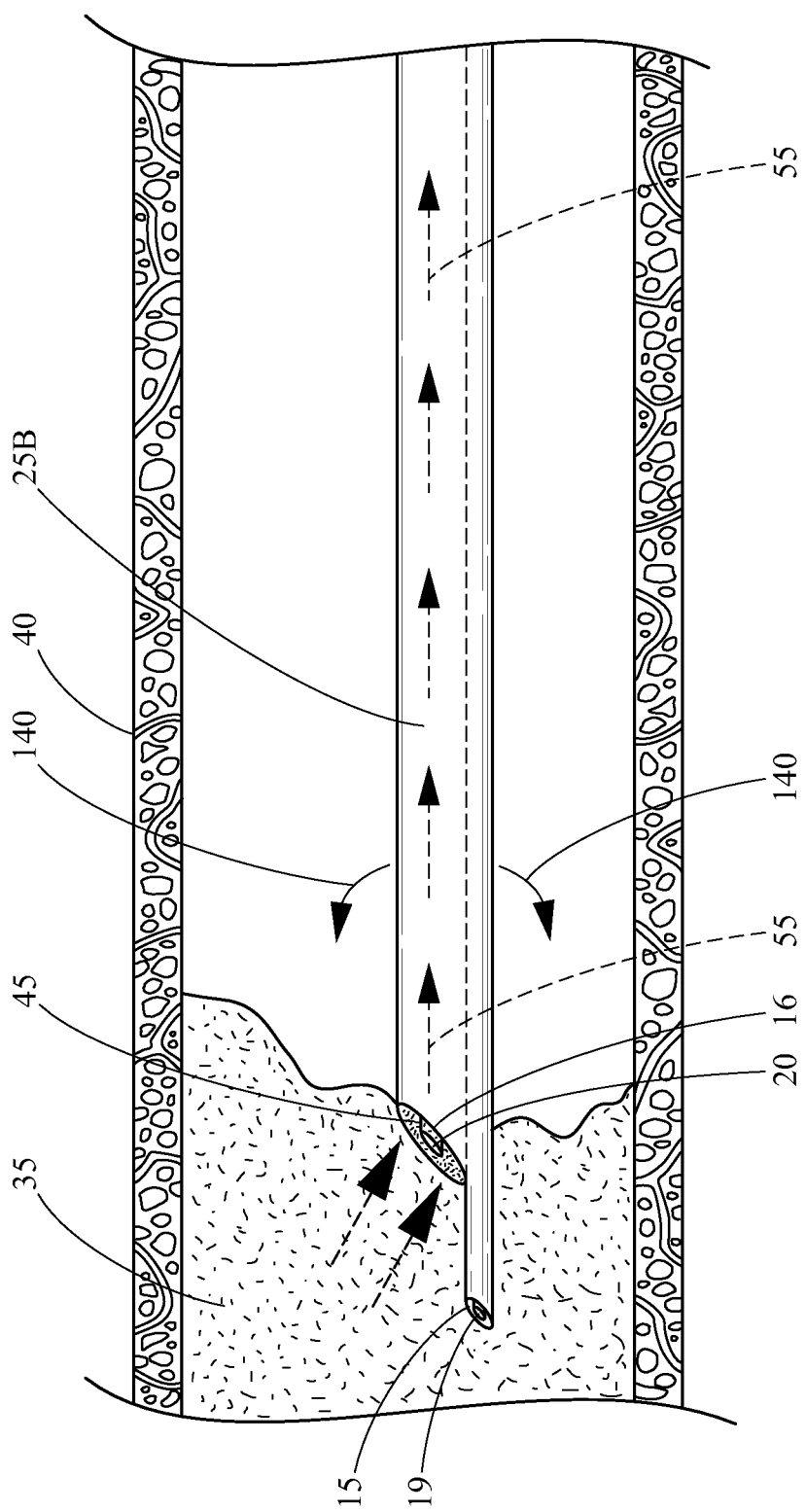

WIRE GUIDED THROMBECTOMY DEVICE

FIELD

This invention relates to medical devices, and more particularly, to devices used to remove thrombus or soft tissue clots from vascular or other lumens.

BACKGROUND

Vascular disease affects a large proportion of individuals each year. One indication of the existence of this disease is the development of a blood clot in the vascular system, which if left untreated may result in deep venous thrombosis, embolisms, or ischemia. These clots, which may either partially or fully occlude a vessel, are usually comprised of an aggregated mixture of thrombus and fibrin.

Various known techniques for the removal of blood clots include both chemical and mechanical treatment. Chemical treatment typically involves the injection of lysing agents into the vessel near the blood clot to chemically attack, dissolve, and disperse the occlusion. Such lysing or thrombolytic agents include plasmin, streptokinase, alteplase, tenecteplase, and reteplase. In this technique, the lysing agent is brought into the proximate vicinity of the blood clot via injection through a cannula or other lumen.

The mechanical treatment of a blood clot typically involves the use of catheters having a rotary cutting head or other form of a rotor/stator homogenizing head. Examples of such rotary devices include rotating burr devices, rotating a helical coil wire within a catheter, and recanalization catheters. Other mechanical devices utilize a sharp point to methodically pummel the occlusion in order to form a hole through it. In each of these cases, although the occlusion is reduced in size or a passageway is created, the residual thrombus/fibrin material resulting from the treatment remains within the vessel.

The removal of residual material formed during the fragmentation of a blood clot is medically desirable. It is further necessary to insure that this residual material does not migrate away from the site of the treatment to other parts of the vessel. Such migration could lead to serious complications, such as embolism, stroke, or a heart attack. The use of a vena cava filter has been employed to catch residual fragments that have migrated from the site of a blood clot. In addition, some mechanical devices have utilized the concept of aspiration to establish or maintain a flow rate through a catheter for the removal of residual thrombus/fibrin material during treatment.

Therefore, there is a need to create a medical device in which the element of the device used to clear an occlusion is shielded from contact with the vessel wall, and in which any resulting residual material may be effectively removed from the vessel.

SUMMARY

The present invention generally provides a medical device for the removal of a thrombus from a blood vessel. In one embodiment, the medical device comprises a tubular outer sheath having a first lumen and a second lumen; a wire guide disposed through the proximal end of the first lumen for delivery of the device into the patient; a laser source disposed through the proximal end of the second lumen that has an optical fiber for ablation of the thrombus into residual material; and a vacuum port coupled to the proximal end of the second lumen for removing any ablated residual material. The distal ends of the first and second lumen are positioned proximate to the thrombus with the ablation of the thrombus occurring within the distal portion of the second lumen near its distal end.

In another embodiment, the optical fiber is positioned within the distal end of the second lumen and supported along the proximal and distal portions of the second lumen by at least one set of support bars. The support bars may be either coupled to the outer surface of the optical fiber, the inner diameter of the second lumen, or both.

In yet another embodiment, the optical fiber is disposed approximate to a predetermined position within the second lumen. The support bars are appropriately spaced by an angle ($\phi$) to maintain the fiber substantially near this predetermined position. The center of the cross-sectional area of the second lumen is preferably selected as the predetermined position.

The number of the support bars in each set may vary with at least three bars being present. The support bars in each set are typically in the same geometric plane, although deviation from this plane is possible. Preferably the angle ($\phi$) between the space bars in each set is less than about 120 degrees.

It is another objective of the present invention to provide a method of removing a thrombus from a blood vessel. This method comprises the steps of introducing a sheath having a plurality of lumens into a blood vessel; inserting a wire guide through one lumen to position the device proximate to a thrombus; positioning a second lumen, which includes an optical fiber, to be proximate to the thrombus; focusing light input from a laser source into the optical fiber; generating laser output at the distal end of optical fiber near the thrombus; applying a vacuum to the second lumen; ablating the thrombus into residual material; and removing the residual material via the applied vacuum.

In another embodiment, the method further comprises the steps of pivoting the second lumen around the first lumen to a location where the thrombus has not yet been ablated; ablating the thrombus into residual material; and removing the residual material via the applied vacuum. These additional steps may be repeated until a substantial portion of the thrombus is removed.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present invention in any way.

FIG. 4 is a schematic view of the distal portion of a thrombectomy device engaged in the removal of a thrombus present in a vessel in accordance with one embodiment of the present invention.

DETAILED DESCRIPTION

Figure 1:
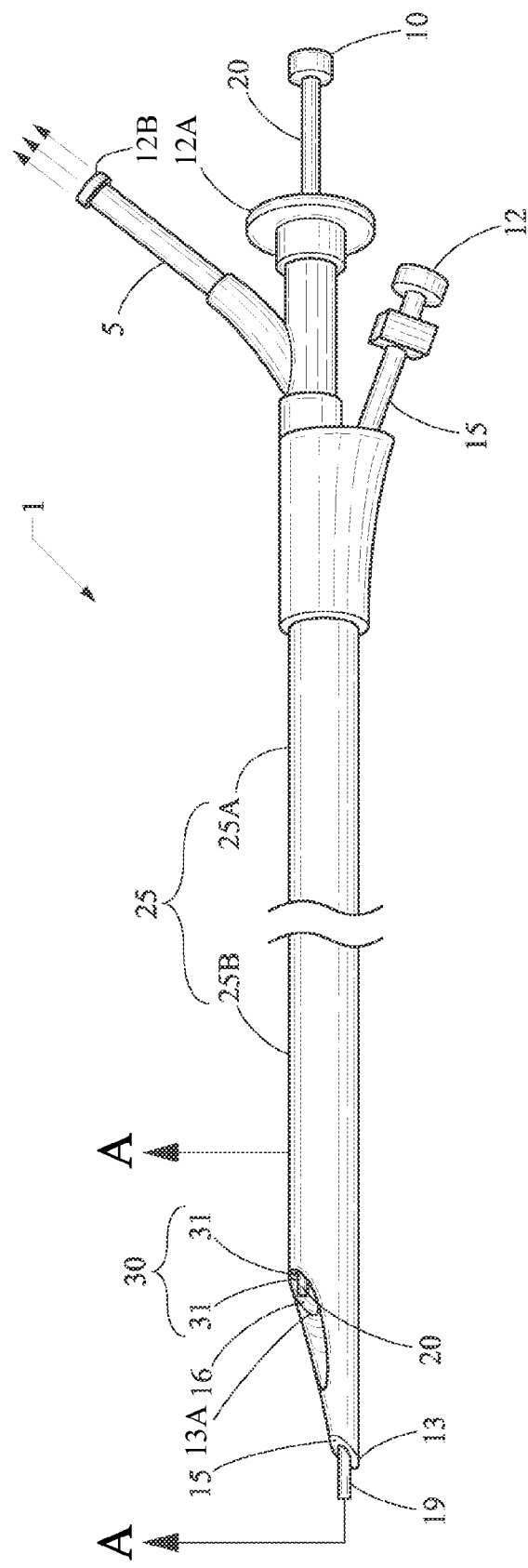
FIG. 1 is perspective view of a thrombectomy device in accordance with one embodiment of the present invention.

The following description is merely exemplary in nature and is in no way intended to limit the present disclosure or its application or uses. It should be understood that throughout the description and drawings, corresponding reference numerals indicate like or corresponding parts and features.

The present disclosure provides a medical device useful for the removal of a thrombus from a blood vessel. Referring to FIG. 1, this medical device (1) comprises a flexible tubular outer sheath (25) that encloses both a first lumen (15) and a second lumen (16) with each lumen having a distal portion (25B) extending to a distal end (13 and 13A, respectively) and a proximal portion (25A) extending from the distal portion (25B) to a proximal end (12, 12A and 12B, respectively).

A wire guide (19) is placed through the proximal end (12) of the first lumen (15) to the distal end (13) of the first lumen (15) for delivery into the patient. A laser source (10) is coupled to an optical fiber (20) and positioned through the proximal end (12A) of the second lumen (16), in order to ablate the thrombus into residual material, the optical fiber (20) being positioned within the distal end (13A) of the second lumen (16) and supported along the proximal and distal portions of the second lumen by at least one set (30) of support bars (31). A vacuum port (5) is coupled to the proximal portion (25A) of the second lumen (16) for removal of any residual material formed during the ablation of the thrombus. During operation of the medical device, the distal ends (13 and 13A) of the first and second lumen (15, 16) are positioned proximate to the thrombus.

The wire guide arrangement in the first lumen (15) includes the use of a hollow needle (not shown) to pierce the patient's skin and enter the body tissue at an angle with respect thereto. A wire guide (19) is then inserted into the hollow needle and is advanced percutaneously into the body tissue to the desired position proximate to the occlusion in the vessel. The hollow needle is then pulled in a backward direction so as to be removed from the body tissue and from contact with the wire guide (19). Next, the thrombectomy device (1) through its first lumen (15) is advanced along the wire guide (19) to a desired position proximate to the thrombus.

The laser ablation of tissue, such as thrombus and fibrin mixture found in a blood clot, is premised on the idea that tissue is mostly water and the vaporization of such tissue is similar to boiling water. Since a gram of water requires a given amount of energy in order to be vaporized, one can calculate the amount of laser energy that needs to be absorbed per unit area at the tissue surface in order to ablate the blood clot. Naturally, process inefficiencies, such as the diffusion of water from underlying wet layers to the point of ablation and the diffusion of heat from the point of ablation to the surrounding tissue needs to be taken into account. During the ablation process, the interaction of the laser with the tissue surface continues to progress deeper into the tissue. In other words, the laser is actually drilling a hole into the tissue during this process.

The laser (10) may be any device that emits highly amplified and coherent radiation of one or more discrete frequencies that behaves as a coherent beam of photons, all in phase and having the similar polarization. Lasers (10) known to one skilled in the art include, but are not limited to, thulium, holmium, erbium argon ion, Nd:YAG, and $CO_2$ type systems. The output of the laser (10) may be applied to the blood clot either continuously or in a pulsed fashion. The wavelength of the output of the laser (10) is preferably either in the near infrared or in the infrared region of the light spectrum.

The output of the laser (10) is transmitted to the thrombus through the use of an optical fiber (20) or waveguide located within the second lumen (16). The composition of this optical fiber may be any composition known to one skilled in the art, such as sapphire or germanium oxide among others. The final determination of the composition of the optical fiber is dependent upon several factors including the wavelength of light that will be transmitted and the degree of flexibility required.

Figure 2:
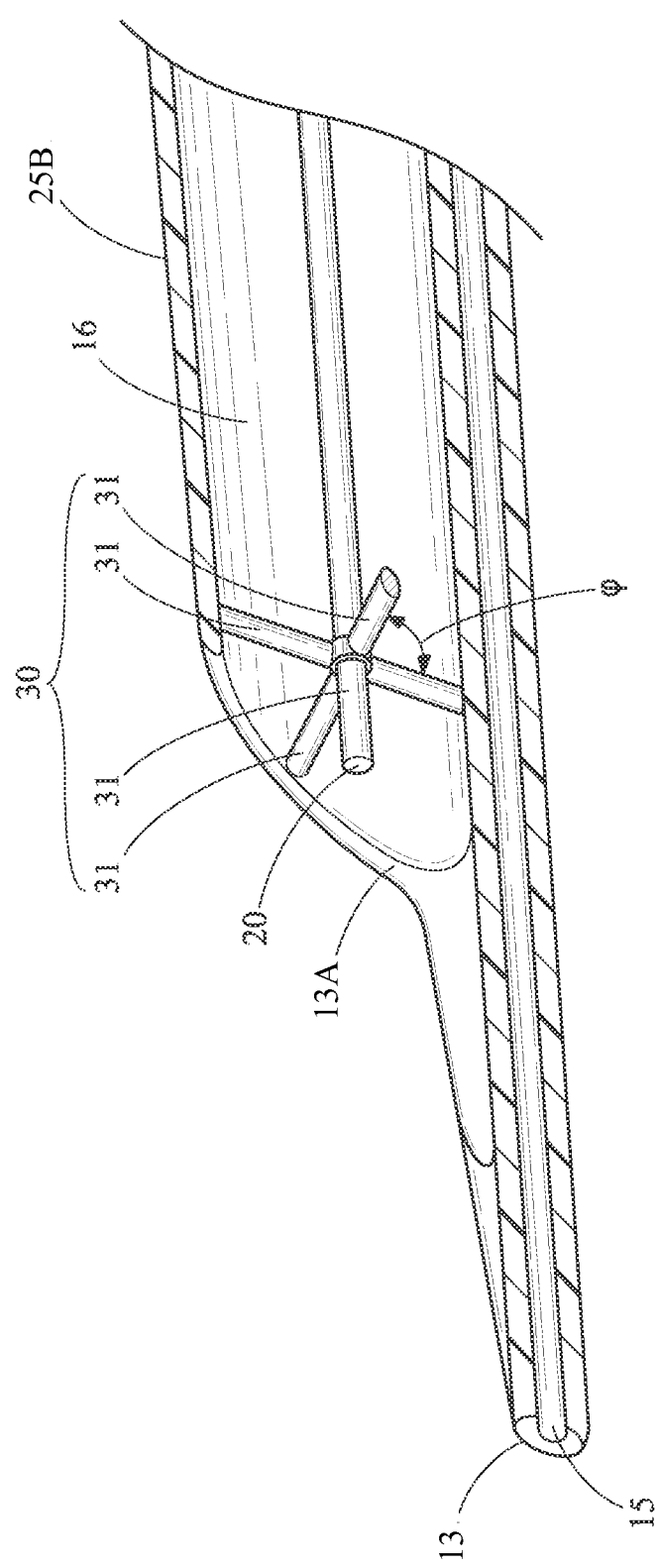
FIG. 2 is an enlarged view of the distal end of the thrombectomy device of FIG. 1 taken along plane A-A

Referring now to FIG. 2, the laser induced ablation of the thrombus into residual material occurs within the distal portion (25B) of the second lumen (16) near its distal end (13A). In other words, the optical fiber (20) ends within the distal portion (25B) of the second lumen (16) near the distal end (13A) of the second lumen. The fiber (20) is supported by at least one set (30) of support bars (31) positioned near the distal end of the optical fiber (20) with the proximal end of the optical fiber (20) being coupled to the laser source (10) or some subcomponent thereof. A plurality of support bar sets (30) may be dispersed throughout the second lumen (16) within the proximal (25A) and distal (25B) portions of the outer sheath (25).

Each set (30) of support bars (31) is comprised of a plurality of support bars (31). In the embodiment of the present invention described in FIG. 2, a total of four support bars (31) is shown to comprise a set (30) of support bars (31). One skilled in the art will realize that the number of support bars (31) in each set (30) may vary. Preferably, the number of support bars (31) in each set (30) is at least three. The support bars (31) in each set (30) are positioned to interact with the outer surface of the optical fiber (20) and the inner diameter of the second lumen (16) at intervals having a spacing that will maintain the fiber (20) substantially near a predetermined position within the second lumen (16). The predetermined position for the fiber (20) is preferably near the center of the cross-sectional area of the second lumen (16) as shown in FIG. 2. However, the predetermined position could be selected to be off-center if desired.

Each of the support bars (31) in a set (30) is preferably arranged to be substantially in the same geometric plane. However, it is feasible that the support bars (31) in a set (30) may be angled so that they are no longer in the same geometric plane. The angle ($\phi$) made between adjacent support bars (31) in a set (30) is dependent upon the number of support bars (31) that make up the set (30). The angle ($\phi$) is typically less than about 120 degrees. When three space bars (31) are present in a set (30), the angle ($\phi$) is preferably about 120 degrees. When four space bars (31) are present in a set (30), the angle ($\phi$) is preferably about 90 degrees.

One end of each support bar (31) may be coupled to the outer diameter of the optical fiber (20) with the other end being proximate to the inner diameter of the second lumen (16). Alternatively, each support bar (30) may be coupled to the inner diameter of the second lumen (16) with the other end being proximate to the outer diameter of the fiber (20). The support bar (30) may alternatively be coupled to both the outer diameter of the fiber (20) and the inner diameter of the second lumen (16).

Figure 3:
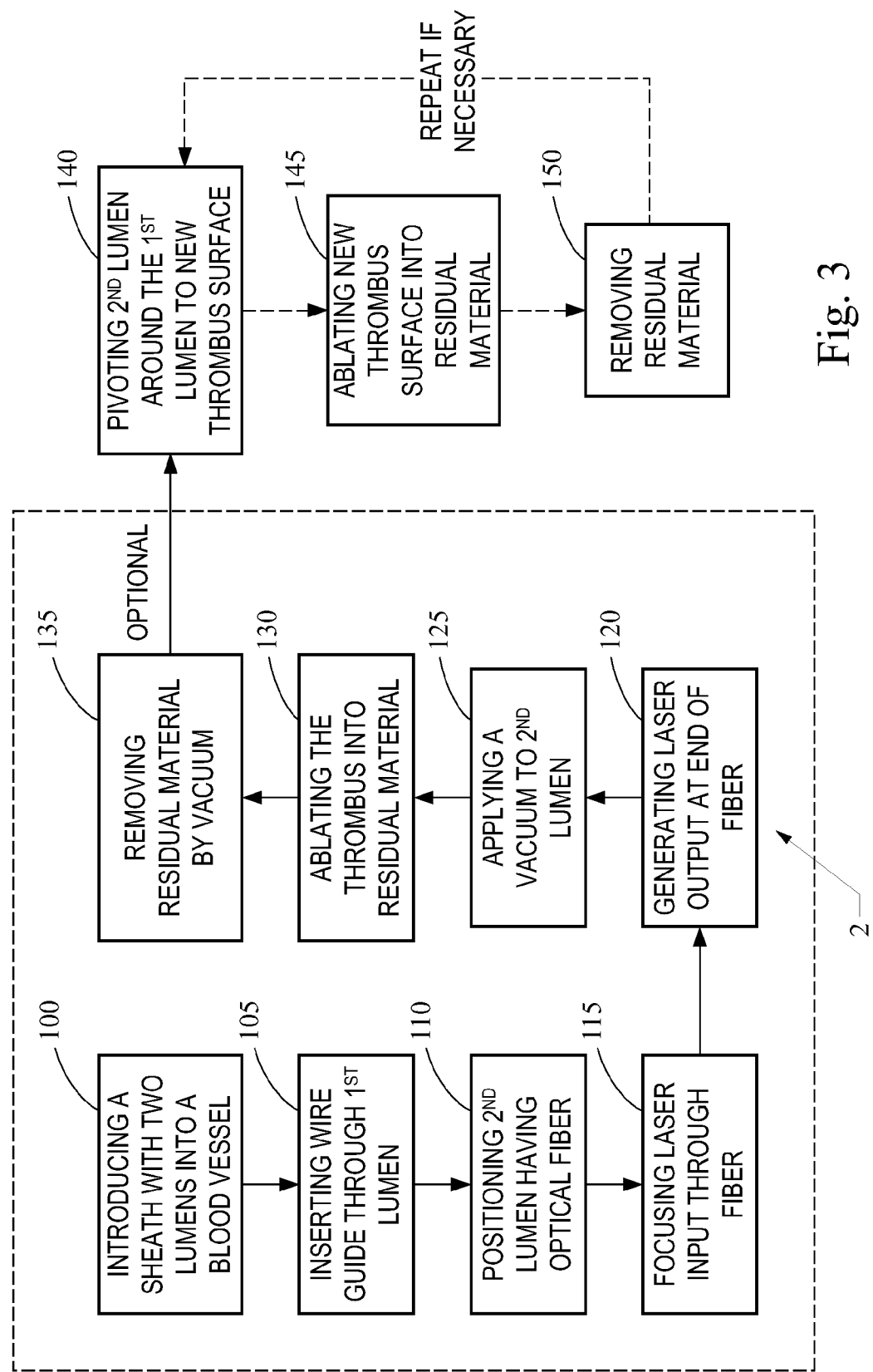
FIG. 3 is a schematic representation of a method for removing a thrombus from a vessel according to one embodiment of the present invention.

It is another objective of the present invention to provide a method (2) for removing a thrombus from a blood vessel. Referring now to FIG. 3, this method comprises the steps of introducing (100) a sheath having a first lumen and a second lumen into a blood vessel; inserting (105) a wire guide through the first lumen to position the distal end of the first lumen proximate to a thrombus; positioning (110) the second lumen proximate to the thrombus; focusing (115) light input from a laser source into an optical fiber; generating (120) a laser output at the distal end of optical fiber; applying a vacuum (125) to the second lumen through a port positioned near the proximal end of the second lumen; ablating (130) the thrombus into residual material with the laser output within the distal portion of the second lumen near its distal end; and removing (135) the residual material via the applied vacuum.

The method of removing a thrombus from a blood vessel may further comprise the steps of pivoting (140) the second lumen around the first lumen to reposition the second lumen proximate to a new portion of the thrombus that has not yet been ablated; ablating (145) the new portion of the thrombus into new residual material with the laser output; and removing (150) the new residual material via the applied vacuum. The steps of pivoting (140) the second lumen, ablating (145) the thrombus, and removing (150) the residual material may be repeated until a substantial portion of the thrombus is removed.

Referring now to FIG. 4, an example in which the distal portion (25B) of a thrombectomy device engaged in an interaction with a thrombus (35) located within a blood vessel (40) is depicted. The wire guide (19) in the first lumen (15) is used to bring the first and second lumen (15, 16) near or proximate to the thrombus. The optical fiber (19) located at the distal end of the second lumen (16) ablates the thrombus (35) creating residual material (45). A vacuum (55) applied through the second lumen (16) assists in the removal of residual material (45).

In addition to removing residual material after ablation takes place, the application of a vacuum (55) may also hold the thrombus (35) in a position at the distal end of the distal portion of the second lumen (16), which may effectively assist the ablation process. As residual material (45) is removed, the ability of the applied vacuum (55) to pull more of the thrombus (35) near the distal end of the second lumen (16) allows for continued ablation of the thrombus (35). The step of pivoting (140) the second lumen (16) around the first lumen (15) further enables the ablation process.

A person skilled in the art will recognize from the previous description that modifications and changes can be made to the present disclosure without departing from the scope of the disclosure as defined in the following claims.

What is claimed is:

1. A method of removing a thrombus from a blood vessel, the method comprising the steps of:
    introducing a sheath having a first lumen and a second lumen into a blood vessel the first lumen and the second lumen each having a distal end, the distal end of the second lumen being proximally offset from the distal end of the first lumen;
    inserting a wire guide through the first lumen to position the distal end of the first lumen in a thrombus;
    positioning the second lumen proximate to the thrombus;
    focusing light input from a laser source into an optical fiber;
    generating laser output at the distal end of the optical fiber;
    applying a vacuum to the second lumen through a port positioned near the proximal end of the second lumen;
    ablating the thrombus into residual material with the laser output within the distal portion of the second lumen near the distal end;
    removing the residual material via the applied vacuum;
    pivoting the second lumen around the first lumen to reposition the second lumen proximate to a new portion of the thrombus that has not yet been ablated;
    ablating the new portion of the thrombus into new residual material with the laser output; and
    removing the new residual material via the applied vacuum.

2. The method of claim 1,
    wherein the steps of pivoting the second lumen, ablating the thrombus, and removing the residual material are repeated until a substantial portion of the thrombus is removed.

3. The method of claim 1, wherein the step of applying a vacuum holds the thrombus in position to be ablated by the laser output within the distal portion of the second lumen near its distal end.

* * * * *